(12) United States Patent
Kraiczek et al.

(10) Patent No.: US 9,752,978 B2
(45) Date of Patent: Sep. 5, 2017

(54) MICROMACHINED FLOW CELL WITH FREESTANDING FLUIDIC TUBE

(75) Inventors: Karsten Kraiczek, Waldbronn (DE); John Mannion, Palo Alto, CA (US); Kevin P. Killeen, Woodside, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 452 days.

(21) Appl. No.: 14/376,430

(22) PCT Filed: Feb. 3, 2012

(86) PCT No.: PCT/EP2012/051878
§ 371 (c)(1),
(2), (4) Date: Aug. 3, 2014

(87) PCT Pub. No.: WO2013/113402
PCT Pub. Date: Aug. 8, 2013

(65) Prior Publication Data
US 2014/0373606 A1 Dec. 25, 2014

(51) Int. Cl.
| | |
|---|---|
| *G01N 21/05* | (2006.01) |
| *B01L 3/00* | (2006.01) |
| *G01N 30/74* | (2006.01) |
| *G01N 33/543* | (2006.01) |
| *B32B 37/18* | (2006.01) |
| *B32B 38/10* | (2006.01) |
| *G01N 21/03* | (2006.01) |
| *G01N 30/02* | (2006.01) |

(52) U.S. Cl.
CPC ........ *G01N 21/05* (2013.01); *B01L 3/502707* (2013.01); *B01L 3/502715* (2013.01); *B32B 37/18* (2013.01); *B32B 38/10* (2013.01); *G01N 30/74* (2013.01); *G01N 33/54373* (2013.01); *B01L 2300/0654* (2013.01); *B01L 2300/0816* (2013.01); *B01L 2300/0838* (2013.01); *B32B 2551/00* (2013.01); *G01N 2021/0346* (2013.01); *G01N 2021/052* (2013.01); *G01N 2021/056* (2013.01); *G01N 2030/027* (2013.01); *G01N 2030/746* (2013.01); *G01N 2201/08* (2013.01); *Y10T 156/10* (2015.01)

(58) Field of Classification Search
CPC ...................................................... G01N 21/05
USPC ....................................................... 73/61.55
See application file for complete search history.

(56) References Cited

U.S. PATENT DOCUMENTS

| | | |
|---|---|---|
| 5,184,192 A | 2/1993 | Gilby et al. |
| 5,423,513 A | 6/1995 | Chervet et al. |
| 6,281,975 B1 | 8/2001 | Munk |
| 6,438,279 B1 | 8/2002 | Craighead et al. |

(Continued)

FOREIGN PATENT DOCUMENTS

| | | |
|---|---|---|
| CN | 1511256 | 7/2004 |
| WO | WO2006007878 | 1/2006 |
| WO | 2010151440 A1 | 12/2010 |

OTHER PUBLICATIONS

Chinese Office action dated Mar. 15, 2016 for Chinese Application No. 201280068989.9.

(Continued)

*Primary Examiner* — Ryan Walsh (57) ABSTRACT

A micromachined flow cell includes a substrate and a freestanding tube, delimiting a fluidic conduit therein and being integrally formed from material of the substrate.

33 Claims, 5 Drawing Sheets

(56) References Cited

U.S. PATENT DOCUMENTS

| | | |
|---|---|---|
| 2002/0187557 A1 | 12/2002 | Hobbs et al. |
| 2002/0194908 A1 | 12/2002 | Sparks |
| 2004/0038426 A1 | 2/2004 | Manalis |
| 2007/0097361 A1 | 5/2007 | Beigel et al. |
| 2011/0203354 A1* | 8/2011 | Yang ................ B01L 3/502761 73/61.72 |

OTHER PUBLICATIONS

International Search Report and Written Opinion mailed Jul. 4, 2012 for Application No. PCT/EP2012/051878.
Office Action mailed Jul. 28, 2015 in Chinese Application No. 201280068989.9 (Unofficial/non-certified translation provided by foreign agent included).
Machine translation of CN 1511256, published Jul. 7, 2004.
International Search Report mailed Jul. 4, 2012 for Application No. PCT/EP2012/051878.
Rusu, et al. "Direct Integration of Micromachined Pipettes in a Flow Channel for Single DNA Molecule Study by Optical Tweezers", Journal of Microelectromechanical Systems, vol. 10, No. 2, Jun. 2001.

* cited by examiner

MICROMACHINED FLOW CELL WITH FREESTANDING FLUIDIC TUBE

BACKGROUND ART

The present application is a national stage application under 35 U.S.C. §371 and claims priority under 35 U.S.C. §121 from International Patent Application No. PCT/EP2012/051878 filed on Feb. 3, 2012. The entire disclosure of International Patent Application No. PCT/EP0122/051878 is specifically incorporated herein by reference.

The present invention relates to a flow cell.

In liquid chromatography, a fluidic analyte may be pumped through conduits and a column comprising a material which is capable of separating different components of the fluidic analyte. Such a material, so-called beads which may comprise silica gel, may be filled into a column tube which may be connected to other elements (like a control unit, containers including sample and/or buffers) by conduits.

When a fluidic sample is pumped through the column tube, it is separated into different fractions. The separated fluid may be pumped in a flow cell in which the different components are identified on the basis of an optical detection mechanism.

U.S. Pat. No. 5,423,513 discloses a method of analyzing fluid samples using a bent capillary flow cell, in which method an external UV/visible light ray beam is directed into an elongated section of the flow cell from a bend thereof, this incident light ray beam is limited to a solid acceptance angle. This solid acceptance angle is determined such that light rays which enter the elongated section traverse predominantly the longitudinal axis thereof, i.e. propagate through the fluid sample, providing an improved signal to noise ratio. Lens means, such as ball lenses, may be used at the entrance and exit side of the elongated section. A bent capillary flow cell is provided, in which the elongated section deviates by an angle from a line perpendicular to a flat side face of a holding template.

U.S. Pat. No. 5,184,192 discloses a flow cell for housing a liquid sample and for exposing a liquid sample to light which comprises a conduit having a smooth inner wall formed of an amorphous fluoropolymer having a refractive index less than the refractive index of water, said amorphous fluoropolymer having a thickness at least as great as the wavelength of light such that when said conduit is filled with water, visible light and ultra-violet light can be transmitted along the axis of said conduit by total internal reflection.

Conventional flow cells may be complex in manufacture.

DISCLOSURE

It is an object of the invention to provide a flow cell which can be manufactured with reasonable effort (particularly flow cells with very low volumes, for instance less than one microliter).

According to an exemplary embodiment of the present invention, a micromachined flow cell is provided which comprises a substrate, and a freestanding tube delimiting a fluidic conduit therein and being integrally formed from material of the substrate.

According to another exemplary embodiment, a fluidic device for measuring a fluidic sample is provided, wherein the fluidic device comprises a processing unit adapted for processing the fluidic sample, and a flow cell having the above mentioned features and being in fluid communication with the processing unit for receiving the processed fluidic sample from the processing unit (particularly for sample detection).

According to still another exemplary embodiment, a method of manufacturing a micromachined flow cell is provided, wherein the method comprises providing a substrate, and integrally forming, from material of the substrate, a freestanding tube delimiting a fluidic conduit therein.

In the context of this application, the term "flow cell" may particularly denote a fluidic conduit delimited by a tubing through which a fluidic sample, which may already be separated, can flow. In the flow cell, electromagnetic radiation may be introduced, and subsequently the fluidic sample may be characterized by detecting the absorption of the electromagnetic radiation by the fluidic sample, or by detecting fluorescence radiation emitted by the fluidic sample upon being excited with primary electromagnetic radiation. The term "electromagnetic radiation" may particularly denote an ensemble of photons. The electromagnetic radiation may be, for instance, in the range of visible light, ultraviolet radiation, or infrared radiation. Primary electromagnetic radiation irradiated onto the fluidic sample and secondary electromagnetic radiation received from the fluidic sample in response to the primary electromagnetic radiation may or may not differ regarding wavelengths. Such primary electromagnetic radiation and such secondary electromagnetic radiation may be monochromatic or polychromatic.

In the context of this application, the term "fluidic sample" may particularly denote any liquid, any gas, any mixture of liquid and gas, optionally comprising solid particles. Such a fluidic sample, for instance a biological sample, may be under analysis, and particularly separated fractions thereof may be detected individually in a flow cell.

In the context of this application, the term "micromachining" may particularly denote a process used to produce microelectromechanical systems (MEMS). Applicable techniques of micromachining include bulk micromachining and surface micromachining. Bulk micromachining defines structures by selectively etching inside a substrate. Surface micromachining uses a succession of thin film deposition and selective etching. Whereas surface micromachining creates structures on top of a substrate, bulk micromachining produces structures inside a substrate. Embodiments of the invention may use bulk micromachining, and optionally surface micromachining. For manufacturing, procedures such as photolithography, dry etching, wet etching, deposition or the like may be applied.

In the context of this application, the term "substrate" may particularly denote a wafer or another solid body, for instance a cuboid or disk, which is processed so as to form a micromachined device with flow cell capability.

In the context of this application, the term "integrally formed from material of the substrate" may particularly denote that the freestanding tube may be formed as an integral part of the processed substrate. Thus, substrate and freestanding tube may be inseparable from one another, i.e. may be separated only by damaging the flow cell.

In the context of this application, the term "freestanding tube" may particularly denote a tube which is formed as a, at least section-wise, free hanging bridge-like structure. Such a freestanding tube may extend horizontally. The freestanding tube may be connected at beginning and end to adjacent bulky substrate portions but may remain free of a continuous or an uninterrupted connection to a lower substrate section.

According to an exemplary embodiment of the invention, a flow cell particularly for a life science apparatuses such as a liquid chromatography device is provided which has a freestanding tube integrally formed of substrate material. Such an arrangement allows for a very compact dimensioning and a robust construction of the flow cell while at the same time preventing leakage and related problems since fluidic interfaces of different materials are avoided due to the integral formation of the flow cell. Furthermore, in view of the air or gas environment surrounding the freestanding tube, the flow cell is appropriate for use as a total internal reflection flow cell in which electromagnetic radiation is reflected at the border between exterior tube surface and surrounding gas environment.

In the following, further exemplary embodiments of the flow cell will be explained. However, these embodiments also apply to the fluidic device and the method.

In an embodiment, the substrate and the freestanding tube consist of the same material, particularly consist of the same chemical composition. This avoids any problems with fluidic interfaces between different materials and with different thermal expansion coefficients.

In an embodiment, the substrate comprises or consists of fused silica. Fused silica is a material which is both optically transparent, capable of being bonded to another body of the same material so as to form the freestanding tube by bonding, as well as capable of forming a fused silica/air interface at which total internal reflection is enabled.

In an embodiment, the freestanding tube is surrounded at least along a section thereof by a gas, particularly by air. By surrounding the tube with a gaseous medium having a low refraction index, total internal reflection occurs at the border between freestanding tube and gas environment, thereby obtaining a total internal reflection cell.

In an embodiment, the fluidic conduit delimited by the freestanding tube has an internal volume in a range between about 1 nl and about 1000 nl, particularly between about 10 nl and about 100 nl. In view of the manufacture of the flow cell by micromachining or micromechanical processes, it becomes possible to manufacture a very compact low flow cell meeting the requirements of modern liquid chromatography devices.

In an embodiment, the substrate has a trench. The freestanding tube may extend along the trench and may be connected to two surface interfaces of the substrate delimiting the trench. By forming the freestanding tube in a trench of a solid substrate, the freestanding tube is located at a hidden position so that it is protected against the environment with regards to mechanical loads acting thereon. Furthermore, by embedding the freestanding tube in a trench, the flow cell may be covered with a cover plate also covering the trench, for improving the mechanical robustness of the flow cell and for simplifying side edge post-processing of the device.

In an embodiment, the freestanding tube between the two surface portions is basically U-shaped. By U-shaping the fluidic conduit it is possible to supply a fluidic sample (which is for instance already separated by a chromatographic device) to a flow cell via a first leg of the U and guiding the fluidic sample after the detection to a destination such as a waste via a parallel second leg of the U. A central portion of the U-shaped fluidic conduit between the two legs can be aligned with and exposed to an electromagnetic radiation path along which electromagnetic radiation may interact with the fluidic sample flowing along the fluidic conduit.

In an embodiment, the substrate has two fluidic channels integrally formed therein, i.e. a supply channel and a drain channel. Each of these fluidic channels may be fluidically coupled, particularly directly fluidically coupled, to a respective one of the two surface portions. Thus, the fluidic conduit within the freestanding tube may continuously pass into the fluidic conduits within the solid substrate.

In an embodiment, each of the two fluidic channels of the substrate ends at a respective one of two fluidic interfaces of the substrate. These fluidic interfaces of the substrate may be located at opposing positions as compared to the connection positions of the two fluidic interfaces of the substrate with the freestanding tube. Such fluidic interfaces may be the fluidic interfaces between the flow cell and connected fluidic components such as chromatographic separation column, waste container or the like. In other words, the fluidic sample may be supplied to the flow cell via one of these fluidic interfaces and may be drained at the other one.

In an embodiment, at least one of the two fluidic interfaces is calotte-shaped. A calotte shape can be obtained by forming the fluidic interfaces by a simple etching procedure. It may be even more preferred to configure the fluidic interfaces as cylindrically shaped bores. Cylindrically shaped bores formed by grinding may allow to significantly reduce the dead volume of the fluidic interfaces.

In an embodiment, the flow cell further comprises a further substrate and a further freestanding tube, particularly a further thin-walled tube, delimiting a further fluidic conduit therein and being integrally formed from material of the further substrate. The substrate and the further substrate may be stacked, for instance by bonding main surface thereof to one another. Hence, a vertical stack of multiple chips may be formed each having an integrated freestanding tube for flow cell applications. This provides for a highly compact arrangement.

In an embodiment, the fluidic conduit of the freestanding tube is fluidically coupled to the further fluidic conduit of the further freestanding tube, i.e. fluid communication may be established between the freestanding tubes. For instance, corresponding fluid coupling ports may be formed at main surfaces of the substrates. In this way, serially coupled flow cells may be formed in a highly compact manner.

In an embodiment, the substrate and the further substrate have the same external contour. Particularly, the substrates may be plate-like structures having the same length and width and/or height. The internal constitution of the two or more stacked substrates may differ, for instance in terms of dimensioning the fluidic conduits therein.

In an embodiment, the flow cell comprises a cover sheet attached to a top surface of the substrate for capping the trench and/or comprises a bottom sheet attached to a bottom surface of the substrate. By use of a cover sheet such as a plate like transparent cover plate, the freestanding tube may be shielded with regard to the environment so as to increase the lifetime of the flow cell. For instance, the sheets may be rigid plates such as glass plates to robustly protect the freestanding tube against external influences. Furthermore, covering the top and/or bottom main surfaces of the trenched substrate with plates significantly simplifies polishing of side surfaces of the device. For instance, one or more of such plates may be made of black glass (i.e. dark stained glass) preventing electromagnetic radiation such as stray light from impinging on the freestanding tube. Alternatively, the sheets may also be embodied as foils such as plastic foils, particularly foils bonded from multiple layers. In such an embodiment, one or more fluidic structures such as fluidic channels may be formed in the bonded multi-layer foil. For instance, this may allow to fluidically couple the device to other similar or different devices, for instance in a device stack.

In an embodiment, the flow cell comprises at least one further freestanding tube delimiting at least one further fluidic conduit therein and being integrally formed from material of the same substrate as the first freestanding tube. Thus, the architecture according to an exemplary embodiment of the invention allows for the provision of multi flow cell arrangements and/or multi fluidic channel configurations, since the integral formation of plural freestanding tubes from one substrate allows for a highly compact device.

In an embodiment, the at least one further fluidic conduit is fluidically connected in series with the first fluidic conduit or parallel to the first fluidic conduit. In a serial connection architecture, it is for instance possible that a fluidic sample first flows to a first fluidic channel of the flow cell and subsequently to a second fluidic channel. In a parallel arrangement, different fluidic samples are guided through different parallel fluidic conduits.

In an embodiment, the at least one further fluidic conduit has another length than the first fluidic conduit so that an effective interaction length along which electromagnetic radiation propagating through the respective fluidic conduit interacts with fluidic sample flowing through the respective fluidic conduit differs for the different fluidic conduits. With the combination of two flow cells having different effective path lengths and both detecting the same fluidic sample (however sequentially in time), the accuracy of the detection may be extended over a larger range which is of particular advantage.

In an embodiment, the freestanding tube and its surrounding are configured (particularly are made of media having appropriate refraction indices) so that an electromagnetic radiation beam propagating through the fluidic conduit is totally reflected at the freestanding tube, particularly at an outer surface of the freestanding tube. Therefore, the flow cell may be configured as a total internal reflection (TIR) flow cell. Total reflection may be advantageous, because this may guarantee that basically all rays used for detection purposes remain within the detection cell and contribute to the detection signal. Total reflection may be denoted as a phenomenon that photons entirely reflect off the surface when the photons propagate from a medium of a high index of refraction towards a medium of a lower index of refraction. For example, total reflection may occur when passing light from glass to air, but not when passing light from air to glass.

In an embodiment, the freestanding tube has an outer surface being shaped as a rectangle, a circle, a hexagon, a polygon with rounded edges, or a shape of two parallel linear sections connected by two opposing curved sections. The outer surface shape of the freestanding tube depends on the manufacturing process, for instance depends on the implemented etching method, particularly whether an isotropic or anisotropic etching procedure is implemented, whether a dry etch or a wet etch process is applied, and which etch chemical is used.

In an embodiment, the freestanding tube has an inner surface being shaped as a rectangle, a circle, or an oval. The inner surface shape of the freestanding tube depends on the manufacturing process, for instance depends on the implemented etching method, particularly whether an isotropic or anisotropic etching procedure is implemented, whether a dry etch or a wet etch process is applied, and which etch chemical is used.

Upon applying deep reactive ion etching, a freestanding tube with a rectangular interior and exterior surface can be obtained. By wet etching (particularly with hydrofluoric acid) the external surface of the freestanding tube may have two straight and two concave sections. A combination of dry etching and wet etching may result in a circular interior surface and a rectangular exterior surface of a freestanding tube.

In an embodiment, the flow cell comprises a first optical coupler element, particularly an optical fiber piece, integrated in the substrate so as to couple electromagnetic radiation via the first optical coupler element into the fluidic conduit. The flow cell may further comprise a second optical coupler element, particularly another optical fiber piece, integrated in the substrate so as to couple electromagnetic radiation from the fluidic conduit into the second optical coupler element. Optic coupler elements (such as waveguides) may allow to convey an electromagnetic radiation beam for interacting with the fluidic sample. Such optical coupler elements may be located at least partially within correspondingly formed recesses of the substrate. Other portions of the optical coupler elements may be located in the trench of the substrate so as to be optically coupled to a central portion of the freestanding tube. Still other portions of the optical coupler elements may be located adjacent to the substrate so as optically connect a light source or a light detector, respectively.

In an embodiment, the flow cell is adapted to conduct a fluidic sample with a high pressure. Such a high pressure may be at least about 50 bar, particularly at least about 100 bar.

In an embodiment, the flow cell is adapted as a microfluidic flow cell. In another embodiment, the flow cell is adapted as a nanofluidic flow cell. Therefore, the system may be specifically configured for microfluidic or nanofluidic applications. The term "microfluidic" may particularly relate to a fluidic device as described herein which allows to convey fluid through microchannels having a dimension in the order of magnitude of less than 500 µm, particularly less than 200 µm, more particularly less than 100 µm or less than 50 µm or less. The term "nanofluidic" may particularly denote a fluidic device as described herein which allows to convey fluid through nanochannels having even smaller dimensions than the microchannels.

The freestanding tube may be optically transparent. In other words, it is possible that the freestanding tube is transparent for electromagnetic radiation in the visible range, i.e. between 400 nm and 800 nm. Additionally or alternatively, it is possible that the freestanding tube is optically transparent for ultraviolet radiation, infrared radiation, or any other wavelength range of electromagnetic radiation used for detection purposes.

The flow cell may comprise an electromagnetic radiation source adapted for generating an electromagnetic radiation beam and for coupling the electromagnetic radiation beam into the fluidic conduit. Such an electromagnetic radiation source may be a light emitting diode, a laser, a light bulb, or any other electromagnetic radiation source having an appropriate emission wavelength or emission wavelength range. Such an electromagnetic radiation may be coupled into the fluidic conduit delimited by the freestanding tube.

The electromagnetic radiation source may be adapted for generating an optical light beam (for instance having a wavelength between about 400 nm and about 800 nm) or an ultraviolet (UV) beam (having shorter wavelengths). The miniature dimensions of the flow cell according to an exemplary embodiment may be appropriate not only for optical applications but also for UV applications, generally for UV-Vis applications.

The flow cell may comprise an electromagnetic radiation detector adapted for detecting the electromagnetic radiation beam after propagation through the fluidic conduit. Such an electromagnetic radiation detector may be arranged to detect light after traveling through the fluidic conduit. Such an electromagnetic radiation detector, for instance a light detector, may comprise a photodiode, a photodiode array or the like capable of generating an electric signal indicative of the corresponding optical signal. It is possible that such an electromagnetic radiation detector comprises a linear or two-dimensional array of photosensitive elements. Such an electromagnetic radiation detector may further comprise additional optical elements such as a grating or the like.

The electromagnetic radiation detector may comprise an optical light detector and/or an ultraviolet radiation detector. The range of sensitivity regarding wavelength of the electromagnetic radiation detector may therefore be adapted to the wavelength of the light used for exciting the system. For instance, the detector may measure electromagnetic radiation absorption by the fluidic sample or electromagnetic radiation fluorescence of the fluidic sample, etc.

In the following, further exemplary embodiments of the fluidic device will be explained. However, these embodiments also apply to the flow cell and the method.

In an embodiment, the processing unit is configured for separating the fluidic sample and is integrated in a chip. More specifically, the chip comprises a plurality of bonded sheets being patterned so as to form a fluidic conduit for conducting the fluidic sample. The arrangement of embodiments of the invention is compatible with a bonded sheet configuration of layers being bonded to one another and forming a chip-like chromatography column. This plate-like arrangement is compatible to a plate-like arrangement of the flow cell according to an exemplary embodiment of the invention. Such a flow cell may be used for an optical detection of fractions of a fluidic sample separated by a chromatographic separation column or the like. The flow cell may be arranged downstream of the separation column.

In an embodiment, a fluidic conduit of the processing unit for conducting the fluidic sample is brought in fluid communication with the fluidic conduit of the freestanding tube via hole-to hole coupling, particularly via vertical hole-to hole coupling. The processing unit and the flow cell may be each formed as planar structures connected to one another at main surfaces of the processing unit and the flow cell so as to provide the hole-to-hole coupling at the connected main surfaces. Such a planar coupling architecture in the context of a hole-to hole coupling scheme is highly efficient and provides for a flat, compact, low dead-volume fluidic device.

The fluidic device may comprise a processing element filled with a separating material. Such a separating material which may also be denoted as a stationary phase may be any material which allows an adjustable degree of interaction with a sample so as to be capable of separating different components of such a sample. The processing element may be arranged in a fluidic path upstream the flow cell detector so that fractions of a sample separated by the processing element may be subsequently detected by the flow cell detector.

The separating material may be a liquid chromatography column filling material or packing material comprising at least one of the group consisting of polystyrene, zeolite, polyvinylalcohol, polytetrafluoroethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 μm to essentially 10 μm. Thus, these beads may be small particles which may be filled inside the separation section of the microfluidic device. The beads may have pores having a size in the range of essentially 50 Å to essentially 300 Å. The fluidic sample may be passed through the pores, wherein an interaction may occur between the fluidic sample and the pores.

The fluidic device may be adapted as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be adapted as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the column. Due to the different interaction of the different protein fractions with the filling of the column (for instance using a liquid chromatography device), the different samples may be distinguished, and one sample or band of material may be selectively isolated as a purified sample.

The fluidic device may be adapted to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and analyzed.

The processing element may be a chromatographic column for separating components of the fluidic sample. Therefore, exemplary embodiments may be particularly implemented in the context of a liquid chromatography apparatus.

In the following, further exemplary embodiments of the method will be explained. However, these embodiments also apply to the flow cell and to the fluidic device.

In an embodiment, the method further comprises providing a first substrate body and a second substrate body, forming a groove in a surface of each of the first substrate body and the second substrate body, and bonding the first substrate body to the second substrate body with the grooves being in mutual alignment so the aligned grooves form the fluidic conduit. The above mentioned substrate is formed by the bonded substrate bodies. Hence, the formation of a fluidic channel buried within the two bonded substrate bodies may form the basis for the subsequently formed freestanding tube.

In an embodiment, the method further comprises forming a trench in the substrate by removing substrate material so that the freestanding tube is constituted by non-removed or remaining material of the substrate. Such a material removal may be performed by an etching procedure such as wet etching or dry etching. Examples are a hydrofluoric acid based etching or a deep ion etching.

In an embodiment, the method further comprises forming two fluidic channels within the substrate and each being fluidically coupled to a respective end of the freestanding tube. There may be a continuous transition between the fluidic channel in the freestanding tube circumferentially surrounded by a gas atmosphere on the one hand and the fluidic channels within the substrate on the other hand. Both the fluidic channel in the freestanding tube as well as the fluidic channels within the substrate may go back to the grooves formed in the cooperating substrate bodies.

In an embodiment, the method further comprises forming, particularly by grinding or etching, spatially extended end sections of the two fluidic channels at positions at which the fluidic channels extend out of the substrate. Etching is a very simple process of forming the interface. Etching may result in calotte shaped interfaces. Grinding has the advantage that it provides for a fluidic interface having a further reduced dead volume. Grinding, for example, allows to form cylindrically shaped fluidic interfaces.

In an embodiment, the flow cell may be manufactured by applying micromechanical manufacturing procedures to one or more fused silica wafers, particularly two wafers may be processed in such a manner that the bonding of these two wafers results later in the formation of the freestanding tube, particularly in combination with a previous suitable etching or grinding procedure for forming grooves.

In an embodiment, the flow cell may be manufactured by firstly etching a first groove in the first fused silica wafer. Secondly, a second groove with a corresponding shape (to the first groove) may be etched in a second fused silica wafer. The two etched fused silica wafers may then be bonded to one another so that the two grooves together form the fluidic channel. A beginning and an end of the channel may then be etched so that calotte shaped interfaces may be formed. Then, the fused silica material of the two fused silica wafers bonded to another may be etched so as to remove fused silica material thereby leaving the freestanding tube freely standing in a hollow trench in the formed fused silica structure.

After having applied a cover plate and/or a bottom plate to the trenched substrate with the freestanding tube therein, it is possible to process wide areas of the plate-shaped flow cell to improve the surface quality. Protection windows may then be formed either on wafer level or on chip level, as required by a certain application.

In an embodiment, a fused silica wafer is micromachined to form a low volume total internal reflection flow cell device. Exemplary features of such a device are a freestanding micromachined fluidic sample detection tube, integrated light waveguides (which may also function as mechanical support structures) connected to the detection tube and side polished windows for coupling light in and out, as well as protection windows for improved mechanical robustness.

Such a flow cell may be appropriate for micro liquid chromatography applications, for instance with a flow rate in a range between 1 µl/min and 100 µl/min. The diameter of the separation columns may be in a range from 100 µm to 1000 µm. A flow cell volume may be in a range between 3 nl and 300 nl. An internal volume of the freestanding tube may be in a range between 1 nl and 1000 nl, particularly 50 nl. The path length, i.e. the length of the freestanding tube between the connected substrate portions may be in a range between 1 mm and 50 mm, particularly in a range between 5 mm and 10 mm. The wall thickness of the freestanding tube may be in a range from 1 µm to 100 µm, for instance may be 10 µm.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

The illustration in the drawing is schematic.

Figure 1:
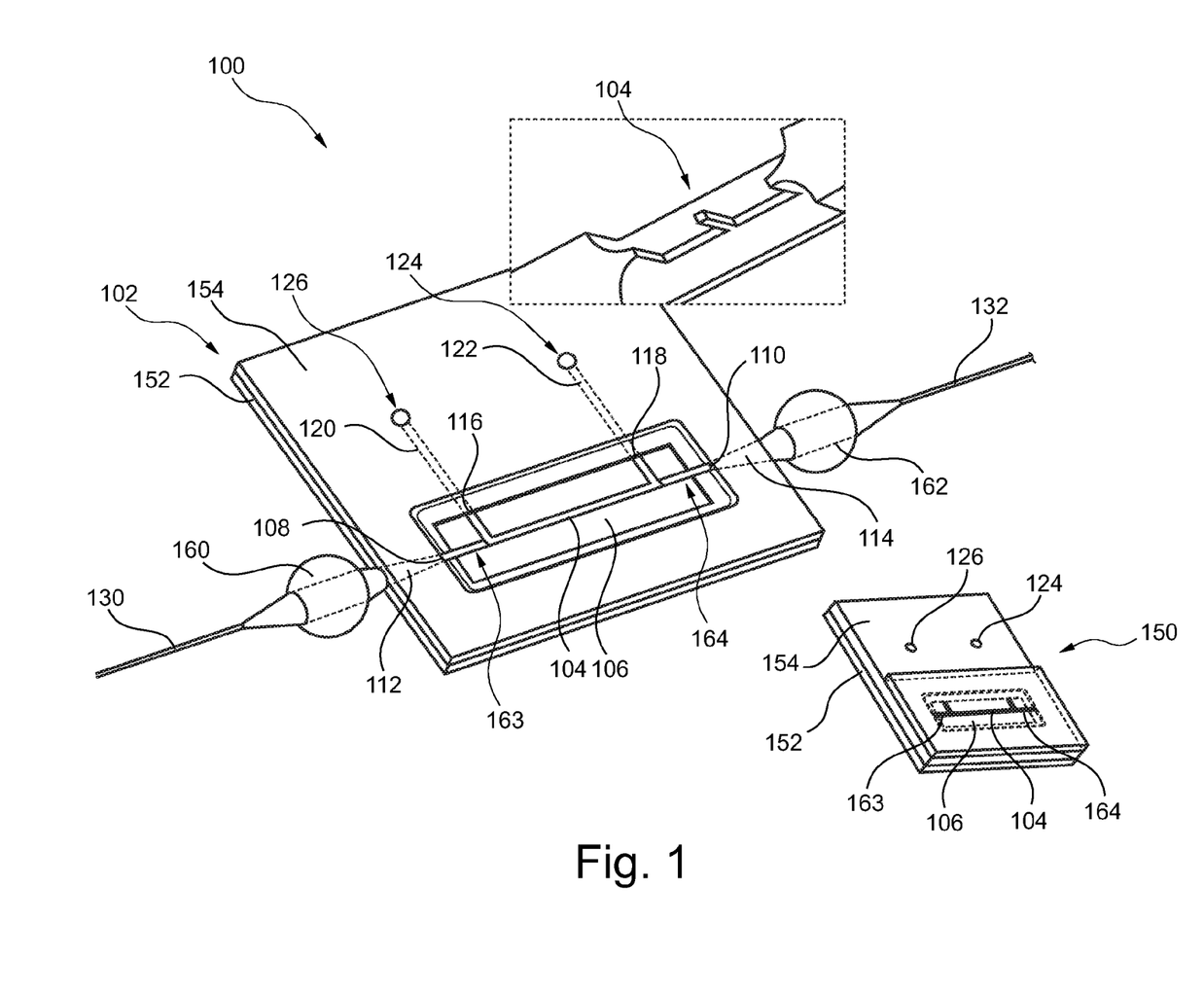
FIG. 1 illustrates a three-dimensional view of a micromachined flow cell according to an exemplary embodiment of the invention together with two details thereof.

FIG. 1 illustrates a micromachined flow cell 100 according to an exemplary embodiment of the invention.

The micromachined flow cell 100 comprises a plate-like substrate 102 made of fused silica material. FIG. 1 shows that the plate-like substrate 102 is constituted by two parallel aligned sub-plates 152, 154 both made of fused silica material and being bonded to one another. The two stacked wafers or sub-plates 152, 154 may for instance have a total thickness of 600 μm or 1050 μm. A fused silica tube 104 stands free, i.e. in a bridge-like manner, along an extension direction which is parallel to the main surfaces of the plate-like substrate 102. The freestanding tube 104 is thin-walled and sealingly delimits in its interior a hollow lumen or fluidic conduit (see reference numeral 800 in FIG. 8). The freestanding tube 104 is circumferentially surrounded by an air atmosphere. The freestanding tube 104 is furthermore integrally formed from fused silica material of the substrate 102 so that the substrate 102 and the freestanding tube 104 are inseparably formed of a single common material.

As can furthermore be taken from FIG. 1, the substrate 102 has a swimming pool-like trench 106, wherein the freestanding tube 104 extends along and within the trench 106 and is connected only at two surface portions 116 and 118 to a vertical wall of the substrate 102 delimiting the trench 106. The freestanding tube 104 is basically U-shaped with two parallel straight legs and a further straight connection portion connecting the two legs to one another. Accordingly, also the lumen within the freestanding tube 104 is basically U-shaped.

Moreover, the fused silica substrate 102 has two integrated and buried fluidic channels 120 and 122 formed therein. Each of the fluidic channels 120 and 122 is directly and seamlessly fluidically coupled via a respective one of the two surface portions 116, 118 to the lumen of the freestanding tube 104. Each of the two fluidic channels 120 and 122 ends at a respective one of two fluidic interfaces 124, 126 at which the buried fluid conduit penetrates an upper surface of the substrate 102. Each of the two fluidic interfaces 124, 126 is a spatially extended end section of the buried fluid conduit and is for example calotte-shaped. A supply capillary (not shown) configured for supplying a fluidic sample to be analyzed by the flow cell 100 is connectable to the fluidic interface 126. This fluidic sample will flow through the fluidic channel 120, the lumen in the freestanding tube 104 and the fluidic channel 122 before leaving the flow cell 100 through the fluidic interface 124 and a drain capillary (not shown) to be connected thereto.

Hence, the fluidic sample takes a basically U-shaped flow path from reference numeral 126 via 120, 104, 122 and 124.

Furthermore, a waveguide 130, a ball lens 160 and a further waveguide 163 are configured for coupling primary light of an appropriate wavelength range into the central section of the lumen of the freestanding tube 104. The primary light is emitted by a light source (not shown). A part of the further waveguide 163 is guided through the substrate 102, see reference numeral 112, and leaves the latter via an interface 108. In a similar way, after the primary light has interacted with the fluidic sample flowing through the central section of the lumen of the freestanding tube 104, the correspondingly generated secondary light propagates through a waveguide 164 (partially guided through the substrate 102, see reference numeral 114), a ball lens 162 and a further waveguide 132 to a light detector (not shown). Thus, the light propagates from light pipe or waveguide 130 through ball lens 160 via interface 108 and light coupler or waveguide 163 into the fluidic channel within the freestanding tube 104, and undergoes total internal reflection at the boundary between an exterior surface of the freestanding tube 104 and the surrounding air environment. Correspondingly, the flow cell 100 comprises optical fiber piece or waveguide 164 which is also partially integrated in the fused silica substrate 102 so as to couple light from the fluidic conduit into optical coupler element or waveguide 132. The secondary light leaves the flow cell 100 via waveguide 164 partly within the substrate 102, via the optional ball lens 162 and via the further waveguide 132 connected to the ball lens 162 for subsequent detection in a detecting element such as one or more photo cells which is not shown in FIG. 1.

A detail of FIG. 1 shows that a cover plate 150 made of an optically transparent material such as glass is attached to the substrate 102 to cover the trench 106 and the freestanding tube 104.

Another detail of FIG. 1 shows the rectangular shape of the freestanding tube 104.

Figure 2:
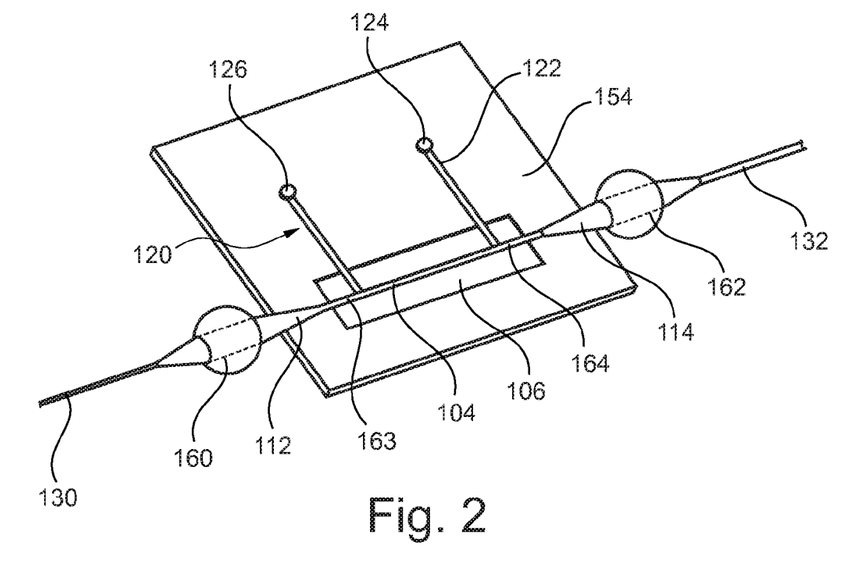
FIG. 2 shows a partially exploded view of the micromachined flow cell of FIG. 1.

FIG. 2 shows the micromachined flow cell 100 of FIG. 1 with detached upper plate 154 to expose the fluidic channels 120, 122.

Figure 3:
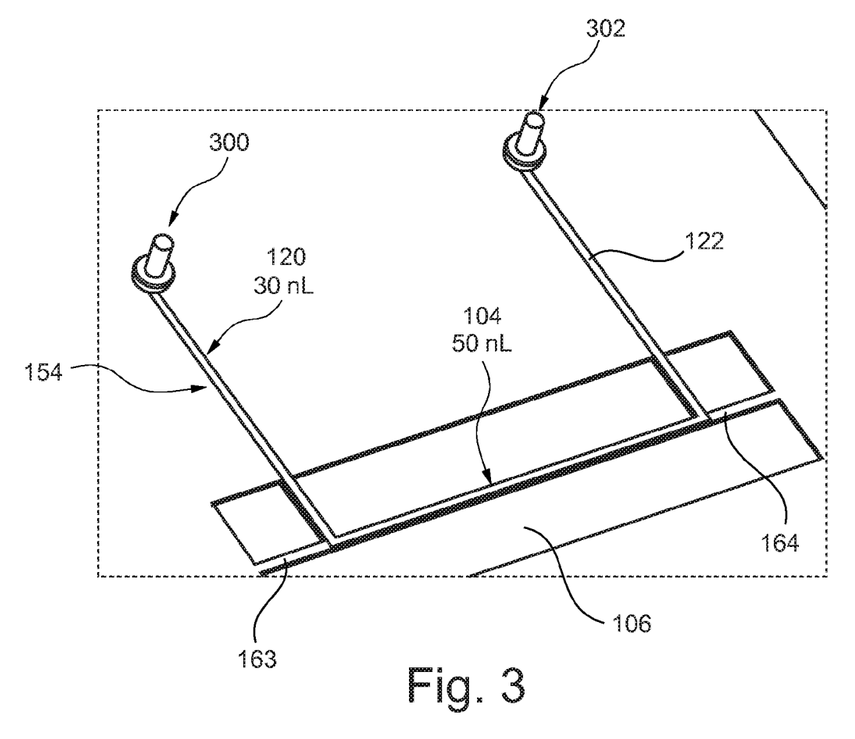
FIG. 3 illustrates a detail of the flow cell of FIG. 1 focusing on the fluidic system of the flow cell.

FIG. 3 shows a further detail of the micromachined flow cell 100 of FIG. 1 and FIG. 2 with internal fluidic volumes. Furthermore, connection plugs 300, 302 are shown as a fluidic interface.

Figures 4A, 4B, 5, 6, 7, 8:
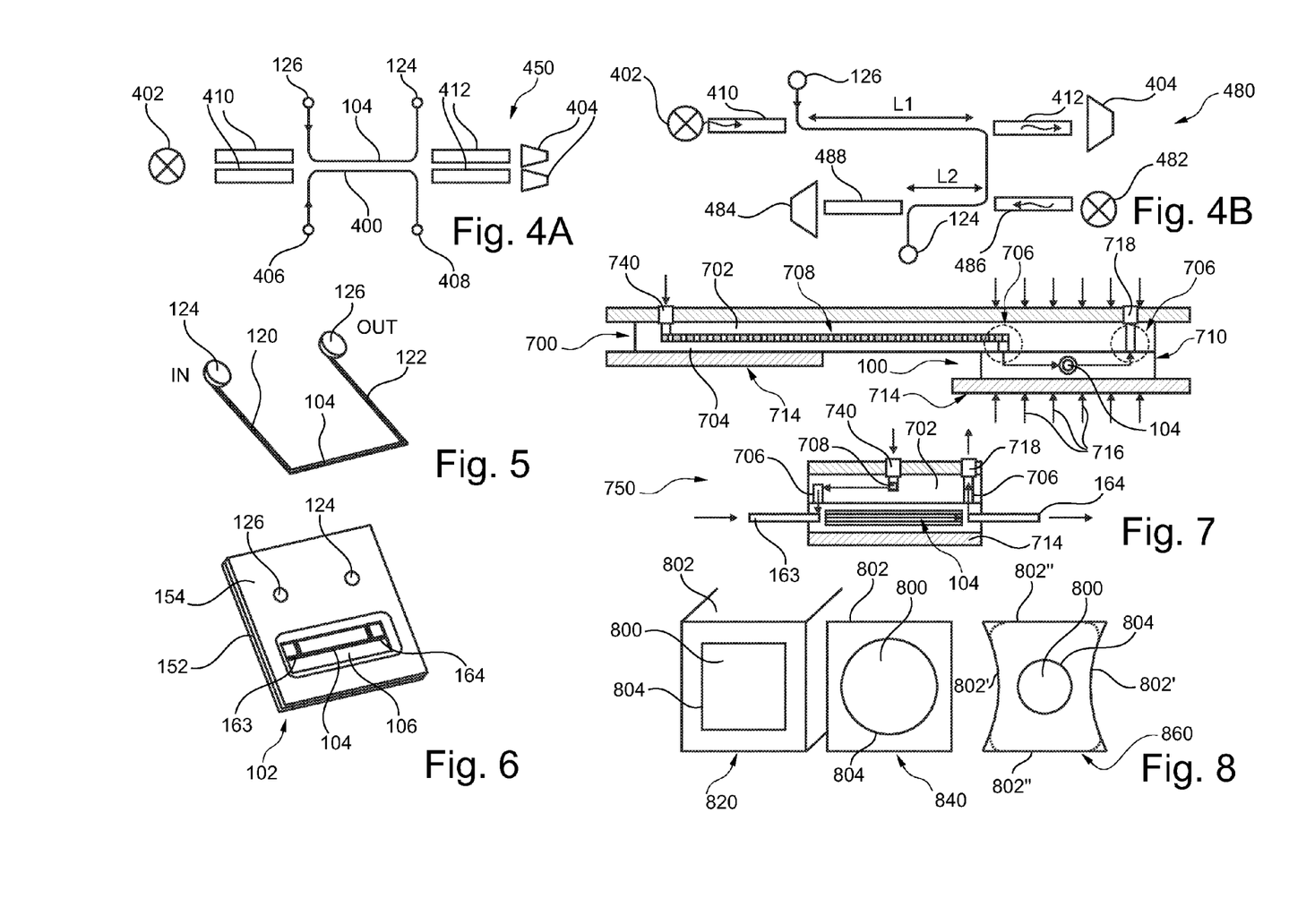
FIG. 4A illustrates a flow cell arrangement according to an exemplary embodiment of the invention in which two fluidic channels are guided in parallel along an electromagnetic radiation path defined by a common light source and a dual light detector.
FIG. 4B illustrates a flow cell according to another exemplary embodiment of the invention in which two fluidic conduits are fluidically coupled in series so as to provide a first flow cell section with an electromagnetic radiation detection path being separate from another electromagnetic radiation detection path of a second flow cell section.
FIG. 5 illustrates a fluidic system of a micromachined flow cell according to an exemplary embodiment of the invention.
FIG. 6 shows a three-dimensional view of a micromachined flow cell according to an exemplary embodiment of the invention.
FIG. 7 illustrates two cross-sectional views of a combined arrangement of a multi-layer chip with integrated chromatographic separation column and a plate-like micromachined flow cell according to an exemplary embodiment of the invention.
FIG. 8 illustrates cross-sectional views of three freestanding tubes according to exemplary embodiments of the invention which may manufactured by applying different etching procedures.

FIG. 4A shows a flow cell arrangement 450 according to another exemplary embodiment of the invention. A first fluidic path is formed by a lumen in a first freestanding tube 104 extending between a fluid inlet port or fluidic interface 126 and a fluid outlet port or fluidic interface 124. In parallel thereto, a second freestanding tube 400 extends between a further fluid inlet port or fluidic interface 406 and a further fluid outlet port or fluidic interface 408. The freestanding tubes 104, 400 extend parallel to one another and have basically parallel electromagnetic radiation detection paths. The latter are formed by an electromagnetic radiation source 402 (two separate electromagnetic radiation sources are possible as well) emitting light or UV radiation to be coupled via a respective one of two supply tubes 410 (for instance in the form of an integrated light pipe) into the freestanding tubes 104, 400. After interaction of this light with already separated fractions of a fluidic sample flowing through a respective one of the freestanding tubes 104, 400, and after total internal reflection of the light at an outer boundary of the freestanding tubes 104, 400 the secondary light is guided via a respective one of two second coupling tubes 412 (for instance in the form of an integrated light pipe) to a respective one of two electromagnetic radiation detectors 404. Although not shown in FIG. 4A, further optical elements such as a grating, deflection mirrors, etc. can be implemented in the optical path. FIG. 4A hence shows a parallel flow cell detection architecture, wherein all detection paths may have the same path length at a relatively small pitch.

In contrast to the parallel fluidic arrangement of FIG. 4A, FIG. 4B illustrates a serial flow cell arrangement 480 according to another exemplary embodiment of the invention. According to FIG. 4B, a first flow cell having a path length L1 is arranged upstream of a second, shorter flow cell with a path length L2<L1. The electromagnetic radiation path lengths of the two flow cells shown in FIG. 4B are different and are defined by electromagnetic radiation source 402, coupling tube 410 (for instance in the form of an integrated light pipe), further coupling tube 412 (for instance in the form of an integrated light pipe) and detector 404 for the first flow cell and are formed by an electromagnetic radiation source 482, a coupling tube 486 (for instance in the form of an integrated light pipe), a further coupling tube 488 (for instance in the form of an integrated light pipe) and a further detector 484 for the second flow cell. By combining a first flow cell having a relatively large path length L1 with a downstream arranged second flow cell having an effective length L2<L1, the range of sensitivity of the entire flow cell arrangement 480 may be extended. The reason for this is that the linear range of accuracy depends on the fluidic path length L1, L2. FIG. 4B shows a tandem flow cell, i.e. a serial arrangement of a large flow cell path length and a short flow cell path length, for an improved linear detection range.

FIG. 5 again shows a fluidic path of the micromachined flow cell 100 of FIG. 1 according to an exemplary embodiment of the invention.

FIG. 6 illustrates an overview of the micromachined flow cell 100 of FIG. 1 without protection cover.

FIG. 7 shows a cross-section of a multi-layer chip 700 integrating a chromatographic separation column 708 and being functionally and structurally connected to a plate-shaped micromachined flow cell 100 according to an exemplary embodiment of the invention. The multi-layer chip 700 comprises a plurality of bonded sheets 702, 704 being patterned so as to form a fluidic conduit 740 for conducting the fluidic sample. Via the fluid outlet channel of the multi-layer chip 700, the fluidic sample with the already separated fractions is supplied for detection in the flow cell 100.

Still referring to FIG. 7, a planar interface between the chip 700 having the chromatographic column 708 and the flow cell 100 is provided. Advantageously, a hole to hole coupling is realized as indicated by reference numeral 706. Such a hole to hole coupling between the chip 700 and the flow cell 100 is provided both at a fluidic input and at a fluidic output of the flow cell 100.

The fluidic sample is supplied via fluidic conduit 740, as sample inlet, and is then separated in chromatographic separation column 708. After separation, the separated fluidic sample is supplied via hole to hole coupling to the flow cell device 100. An interface 710 between the separation chip 700 and the micromachined flow cell 100 may be realized by a microfluidic polymer structure. The arrangement of coupled components 700, 100 may be attached to a support such as an instrument hardware 714. Pressure seal forces are indicated schematically with reference numeral 716. After detection in the flow cell 100, the fluidic sample may be drained via drain hole 718.

A side view 750 of the coupled separation chip 700 and micromachined flow cell 100 is also shown in FIG. 7. Here, a direct fiber coupling without ball lenses is shown. Alternatively, one or more ball lenses may be implemented as well in FIG. 7.

FIG. 8 shows three different cross-sectional views of interior and exterior shapes of freestanding tubes delimiting a lumen 800. A desired embodiment of FIG. 8 can be selected by correspondingly adjusting the used etching procedure.

A first embodiment 820 shown in FIG. 8 has an outer surface 802 shaped like a rectangle or square. An inner surface 804 is shaped as a rectangle or square as well.

A second embodiment 840 shown in FIG. 8 has an outer surface 802 shaped as a rectangle or square and an inner surface 804 shaped as a circle or oval.

A third embodiment 860 of FIG. 8 has an outer surface consisting of two parallel linear sections 802" connected by two opposing curved sections 802', and have an inner surface 804 shaped as a circle. The sharp exterior edges may be rounded by appropriate processing (particularly by etching), as indicated in FIG. 8 with dotted lines.

Figures 9, 10, 11, 12:
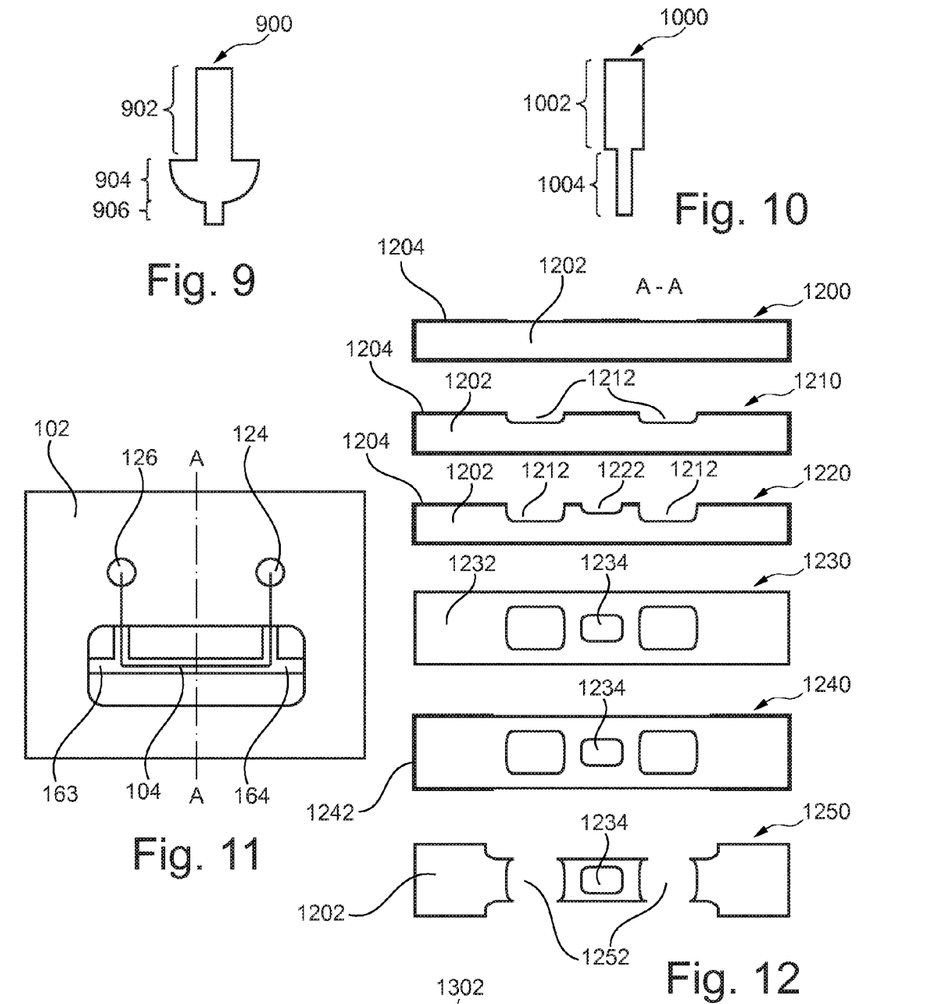
FIG. 9 illustrates a calotte-shaped fluidic interface between a micromachined flow cell according to an embodiment of the invention and a fluidic environment.
FIG. 10 illustrates a cylindrically-shaped fluidic interface between a micromachined flow cell according to an embodiment of the invention and a fluidic environment.
FIG. 11 is a plan view of a micromachined flow cell according to an exemplary embodiment of the invention defining an axis A-A.
FIG. 12 illustrates different cross-sections of fused silica wafers processed during the manufacture of a micromachined flow cell according to an exemplary embodiment of the invention.

FIG. 9 shows an example of a shape of a fluidic interface as the one denoted with reference numeral 706 above. The shown fluidic interface 900 has a first cylindrical section 902, a directly connected calotte shaped section 904 and a further cylindrical section 906. The embodiment of FIG. 9 can be obtained by an etching procedure. The first cylindrical section 902 relates to the separation chip 700, whereas the calotte shaped section 904 and the further cylindrical section 906 relate to the micromachined flow cell 100.

FIG. 10 shows another example of a shape of a fluidic interface as the one denoted with reference numeral 706 above. This fluidic interface 1000 between an integrated flow cell and a fluidic environment has a first cylindrical section 1002 and a directly connected second cylindrical section 1004 having a different, here smaller, diameter than the first cylindrical section 1002. The embodiment of FIG. 10 can be manufactured by grinding material of the substrate and has the advantage of a low dead volume and a better purged volume. The first cylindrical section 1002 relates to the separation chip 700, whereas the second cylindrical section 1004 relates to the micromachined flow cell 100.

FIG. 11 shows a plan view of an integrated flow cell according to an exemplary embodiment which is very similar to the one shown in FIG. 1. A line A-A is defined in FIG. 11.

The various cross-sections shown in FIG. 12 are taken along this line A-A. These cross-sections relate to semi-finished products as obtained during a manufacturing process of producing a micromachined flow cell according to an exemplary embodiment of the invention. This process will be explained in the following in further detail.

FIG. 12 shows a first cross-sectional view 1200 of a fused silica substrate 1202 being covered partially with a protection mask 1204 on specific surface portions thereof. The protection mask 1204 is patterned at an upper main surface of the substrate 1202.

In order to obtain cross-sectional view 1210, an etching process is applied which removes material from surface portions of the substrate 1202 which are not protected by protection mask 1204. Cross-sectional view 1210 therefore shows the structure after a hydrofluoric acid (HF) etch of the exposed area. This procedural step can be used for defining wall thickness.

As can be taken from cross-sectional view 1220, a further patterning procedure may expose another surface portion of the substrate 1202, i.e. may selectively remove material of the protection mask 1204. Subsequently, an etching procedure may be performed so as to form two deep grooves 1212 and one shallow groove 1222 in between.

Starting from the structure according to the cross-sectional view 1220, the remaining protection mask 1204 may be removed by selective etching.

The cross-sectional view 1230 can be obtained by bonding two substrates according to cross-sectional view 1220 (after removal of protection mask 1204) to one another. This forms interior fluidic channel 1234.

Cross-sectional view 1240 is obtained from cross-sectional view 1230 by covering and opening lateral surface portions of the substrate 1202 with protection mask 1242.

A subsequent etching process (HF-etching) defines a freestanding tube in a center separated from other remaining portions of the substrate 1202. Cross-sectional view 1250 shows the obtained structure after removal of the protection mask. Singularization of the individual structures may be carried out as well.

The geometry of the freestanding tube of FIG. 12 is obtained by wet etching.

Figures 13, 14:
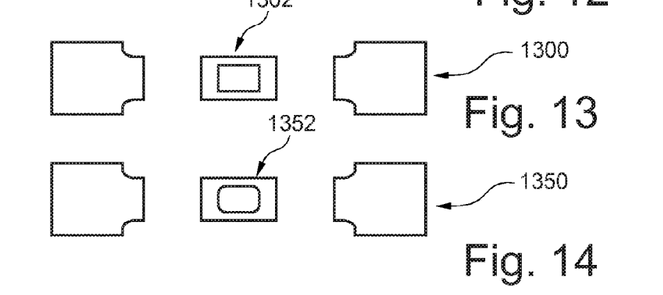
FIG. 13 is a cross-sectional view of a micromachined flow cell according to an exemplary embodiment of the invention in which the freestanding tube has a rectangular interior surface and a rectangular exterior surface.
FIG. 14 is a cross-sectional view of a micromachined flow cell according to another exemplary embodiment of the invention having a rounded rectangular or basically oval interior cross-section and a rectangular exterior cross-section.

FIG. 13 shows that a freestanding tube 1302 can have another shape when other etching procedures are applied. The shape according to FIG. 13 can be obtained by applying DRIE (Deep Reactive Ion Etching) for detection tube and release area, wherein a HF-etch can be used for a final release etching.

FIG. 14 shows a freestanding tube 1352 with still another shape obtained by applying still a further etching procedure. To obtain the shape according to FIG. 14, a wet etch procedure is applied for an inner contour and DRIE is applied for an outer contour of the detection tube. The final release etch is carried out by a HF-etch.

Figure 15:
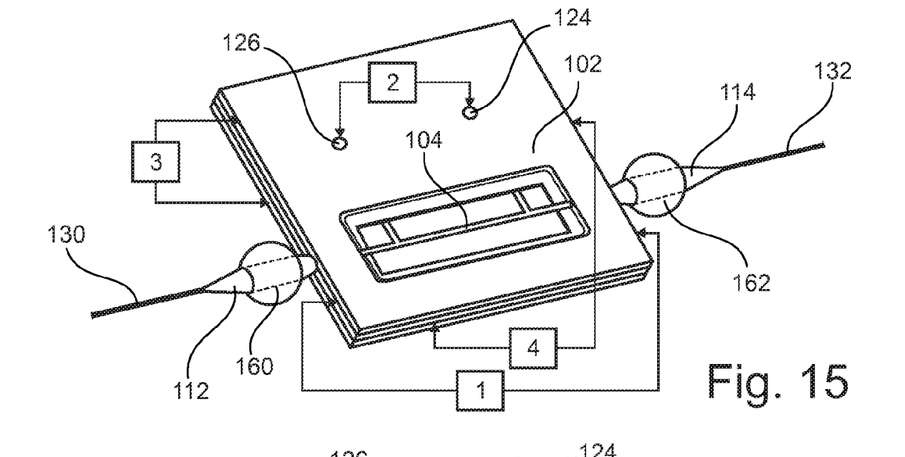
FIG. 15 is an overview of a micromachined flow cell according to an exemplary embodiment of the invention showing characteristic features thereof.

FIG. 15 shows another view of the micromachined flow cell 100 of FIG. 1 in which several features are highlighted. Feature 1 shows side machining of optical windows for coupling light in and out. Feature 2 shows machining of low dead volume fluidic access holes. Feature 3 shows bonding of protection windows for improved mechanical robustness. Feature 4 shows machining of mechanical references for easy exchange of flow cell devices.

Figure 16:
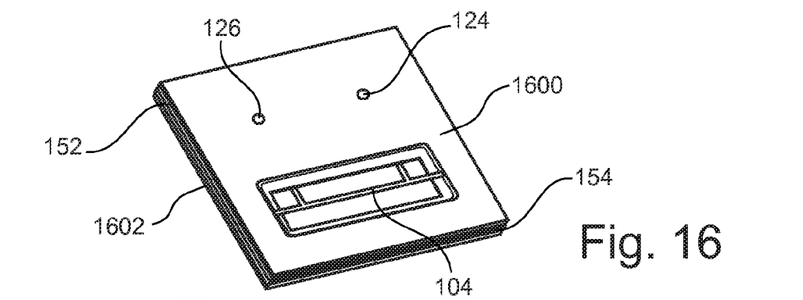
FIG. 16 and FIG. 17 illustrate coverage of a flow cell according to an exemplary embodiment of the invention with cover plates.

FIG. 16 shows as to how a cover plate 1600 is attached and connected to an upper surface of the micromachined flow cell 100 and as to how a bottom plate 1602 is attached and connected to a lower surface of the micromachined flow cell 100. Furthermore, protection windows are formed.

Figure 17:
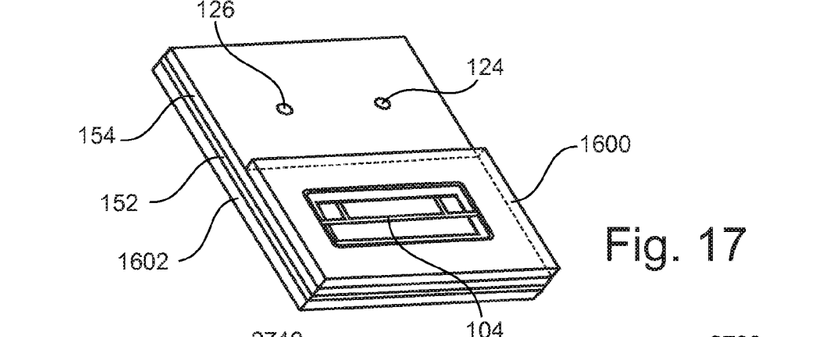

FIG. 17 shows that only a portion of the upper surface of the micromachined flow cell is covered with the cover plate 1600.

Figure 18:
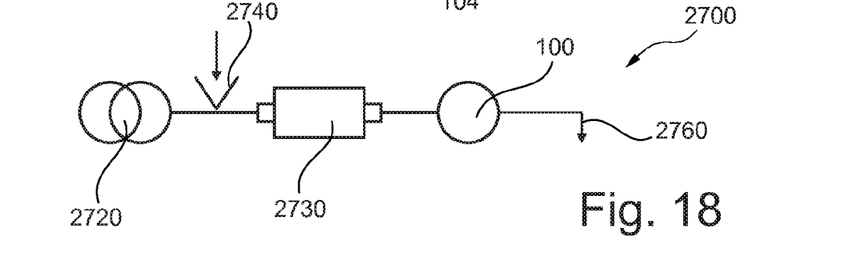
FIG. 18 is a liquid chromatography device having implemented a micromachined flow cell according to an exemplary embodiment of the invention.

FIG. 18 depicts a general schematic of a liquid separation system 2700. A pump 2720—as a mobile phase drive—drives a mobile phase through a separating device 2730 (such as a chromatographic column) comprising a stationary phase. A sampling unit 2740 can be provided between the pump 2720 and the separating device 2730 in order to introduce a sample fluid to the mobile phase. The stationary phase of the separating device 2730 is adapted for separating compounds of the sample liquid. A flow cell 100 as part of a detector is provided for detecting separated compounds of the sample fluid. A fractionating unit 2760 can be provided for outputting separated compounds of sample fluid.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A flow cell, comprising:
a substrate; and
a freestanding tube delimiting a fluidic conduit therein and being integrally formed from material of the substrate, and surrounded by a gas atmosphere,
wherein the freestanding tube comprises a section comprising a first end and a second end, and the section is configured for receiving electromagnetic radiation at the first end, and for emitting at the second end electromagnetic radiation having propagated through the fluidic conduit, and wherein the electromagnetic radiation coupled into the fluidic conduit undergoes total internal reflection at a boundary between an exterior surface of the freestanding tube and the surrounding gas atmosphere.

2. The flow cell according to claim 1, wherein the substrate and the freestanding tube are composed of the same material.

3. The flow cell according to claim 1, wherein the substrate comprises fused silica.

4. The flow cell according to claim 1, wherein the fluidic conduit has an internal volume in a range selected from the group consisting of: between 1 nl and 1000 nl, and between 10 nl and 100 nl.

5. The flow cell according to claim 1, wherein the substrate comprises a trench and two surface portions, and the freestanding tube extends along the trench and is connected to the two surface portions of the substrate delimiting the trench.

6. The flow cell according claim 5, wherein the freestanding tube between the two surface portions is U-shaped.

7. The flow cell according claim 5, wherein the substrate comprises two fluidic channels formed therein, and wherein each of the fluidic channels is directly fluidically coupled to a respective one of the two surface portions.

8. The flow cell according claim 7, wherein each of the two fluidic channels ends at a respective one of two fluidic interfaces of the substrate.

9. The flow cell according claim 8, wherein at least one of the two fluidic interfaces is spatially extended compared to the respective one of the two fluidic channels.

10. The flow cell according to claim 5, comprising a feature selected from the group consisting of: a cover sheet attached to a top surface of the substrate for capping the trench; a bottom sheet attached to a bottom surface of the substrate; and both of the foregoing.

11. The flow cell according to claim 1, further comprising a further substrate and a further freestanding tube delimiting a further fluidic conduit therein and being integrally formed from material of the further substrate, wherein the substrate and the further substrate are vertically stacked.

12. The flow cell according to claim 11, wherein the fluidic conduit is fluidically coupled to the further fluidic conduit.

13. The flow cell according to claim 11, wherein the substrate and the further substrate have the same external contour.

14. The flow cell according to claim 1, comprising at least one further freestanding tube delimiting at least one further fluidic conduit therein and being integrally formed from material of the same substrate as the freestanding tube.

15. The flow cell according to claim 14, wherein the at least one further fluidic conduit is fluidically connected in series with the fluidic conduit or is fluidically connected in parallel to the fluidic conduit.

16. The flow cell according to claim 14, wherein the at least one further fluidic conduit has another length than the fluidic conduit so that an effective interaction length (L1, L2) along which electromagnetic radiation propagating through the respective fluidic conduit interacts with a fluidic sample flowing through the respective fluidic conduit differs for the different fluidic conduits.

17. The flow cell according to claim 1, wherein the exterior surface the freestanding tube has a shape selected from the group consisting of: a rectangle, a circle, a hexagon, a polygon with rounded edges, and a shape of two parallel linear sections connected by two opposing curved sections.

18. The flow cell according to claim 1, wherein the freestanding tube comprises an inner surface having a shape selected from the group consisting of: a rectangle, a rectangle having rounded edges, a circle, and an oval.

19. The flow cell according to claim 1, comprising a feature selected from the group consisting of:
the flow cell comprises a first optical coupler element at least partially integrated in the substrate so as to couple electromagnetic radiation via the first optical coupler element into the fluidic conduit;
the flow cell comprises a second optical coupler element at least partially integrated in the substrate so as to couple electromagnetic radiation from the fluidic conduit into the second optical coupler element; and
both of the foregoing.

20. The flow cell according to claim 1, comprising an electromagnetic radiation source adapted for generating an electromagnetic radiation beam and for coupling the electromagnetic radiation beam into the fluidic conduit.

21. The flow cell according to claim 20, comprising a feature selected from the group consisting of:
the electromagnetic radiation source is configured for generating an optical light beam or an ultraviolet beam;
the flow cell comprises an electromagnetic radiation detector configured for detecting the electromagnetic radiation beam after propagation through the fluidic conduit;
the flow cell comprises an electromagnetic radiation detector configured for detecting the electromagnetic radiation beam after propagation through the fluidic conduit wherein the electromagnetic radiation detector comprises an optical light detector or an ultraviolet radiation detector; and
a combination of two or more of the foregoing.

22. The flow cell according to claim 1, a feature selected from the group consisting of:
the material of the freestanding tube is optically transparent;
the flow cell is configured to conduct a fluidic sample with a high pressure;
the flow cell is configured to conduct a fluidic sample with a pressure of at least 50 bar;
the flow cell is configured to conduct a fluidic sample with a pressure of at least 100 bar;
the flow cell is configured to conduct a liquid sample;
the flow cell is configured as a microfluidic flow cell;
the flow cell is configured as a nanofluidic flow cell; and
a combination of two or more of the foregoing.

23. A fluidic device for measuring a fluidic sample, the fluidic device comprising:
a fluid separating device configured for separating the fluidic sample; and
a flow cell according to claim 1 in fluid communication with the fluid separating device and configured for receiving the separated fluidic sample from the fluid separating device.

24. The fluidic device according to claim 23, wherein the fluid separating device is integrated in a chip.

25. The fluidic device according to claim 24, wherein the chip comprises a plurality of bonded sheets being patterned so as to form a fluidic conduit for conducting the fluidic sample.

26. The fluidic device according to claim 23, wherein a fluidic conduit of the fluid separating device is configured for conducting the fluidic sample, and is brought in fluid communication with the fluidic conduit of the freestanding tube via a hole-to hole coupling.

27. The fluidic device according to claim 26, wherein the fluid separating device and the flow cell are each formed as planar structures connected to one another at main surfaces of the fluid separating device and the flow cell so as to provide the hole-to-hole coupling at the connected main surfaces.

28. The fluidic device according to claim 23, comprising a feature selected from the group consisting of:
the fluid separating device is configured for retaining the fluidic sample being a part of a mobile phase and for allowing other components of the mobile phase to pass the fluid separating device;
the fluid separating device comprises a chromatographic column for separating components of the fluidic sample;
at least a part of the fluid separating device is filled with a fluid separating material;
at least a part of the fluid separating device is filled with a fluid separating material, wherein the fluid separating material comprises beads having a size in the range of 1 µm to 10 µm;
at least a part of the fluid separating device is filled with a fluid separating material, wherein the fluid separating material comprises beads having pores having a size in the range of 50 Å to 300 Å;
the flow cell is arranged downstream of the fluid separating device;
the fluid separating device comprises a microstructured body and porous material covering at least a portion of a surface of the microstructured body;
the fluidic device is configured as a fluid separation system for separating compounds of the fluidic sample;
the fluidic device is configured to analyze at least one physical, chemical and/or biological parameter of at least one compound of the fluidic sample;
the fluidic device comprises a device selected from the group consisting of: a sensor device, a test device for testing a device under test or a substance, a device for chemical, biological and/or pharmaceutical analysis, a capillary electrophoresis device, a liquid chromatography device, and an HPLC device,
a gas chromatography device, and
a gel electrophoresis device.

29. A method of manufacturing a flow cell by micromachining, the method comprising:
providing a substrate;
integrally forming, from material of the substrate, a freestanding tube such that the freestanding tube is surrounded by a gas atmosphere; and
delimiting a fluidic conduit in the freestanding tube,
wherein the freestanding tube comprises a section comprising a first end and a second end, and the section is configured for receiving electromagnetic radiation at the first end, and for emitting at the second end electromagnetic radiation having propagated through the fluidic conduit, and wherein the electromagnetic radiation coupled into the fluidic conduit undergoes total internal reflection at a boundary between an exterior surface of the freestanding tube and the surrounding gas atmosphere.

30. The method according to claim 29, wherein the method further comprises:
   providing a first substrate body and a second substrate body;
   forming a groove in each of the first substrate body and the second substrate body;
   bonding the first substrate body to the second substrate body with correspondingly aligned grooves so as to form the fluidic conduit by the aligned grooves and so as to form the substrate by the bonded substrate bodies.

31. The method according to claim 30, wherein the method further comprises forming a trench in the substrate by removing material of the substrate in such a way that the freestanding tube is constituted by non-removed material of the substrate.

32. The method according to claim 29, wherein the method further comprises forming two fluidic channels within the substrate and each being fluidically coupled to a respective end of the freestanding tube.

33. The method according to claim 32, wherein the method further comprises forming spatially extended end sections of the two fluidic channels at positions at which the fluidic channels extend out of the substrate.

\* \* \* \* \*